(12) United States Patent
Deng et al.

(10) Patent No.: US 11,398,642 B2
(45) Date of Patent: Jul. 26, 2022

(54) NON-AQUEOUS ELECTROLYTE FOR LITHIUM ION BATTERY AND LITHIUM ION BATTERY

(71) Applicant: SHENZHEN CAPCHEM TECHNOLOGY CO., LTD., Guangdong (CN)

(72) Inventors: Zhaohui Deng, Guangdong (CN); Shiguang Hu, Guangdong (CN); Muchong Lin, Guangdong (CN); Qiao Shi, Guangdong (CN)

(73) Assignee: SHENZHEN CAPCHEM TECHNOLOGY CO., LTD., Shenzhen (CN)

( * ) Notice: Subject to any disclaimer, the term of this patent is extended or adjusted under 35 U.S.C. 154(b) by 382 days.

(21) Appl. No.: 16/610,905

(22) PCT Filed: Jun. 23, 2017

(86) PCT No.: PCT/CN2017/089664
§ 371 (c)(1),
(2) Date: Nov. 4, 2019

(87) PCT Pub. No.: WO2018/218714
PCT Pub. Date: Dec. 6, 2018

(65) Prior Publication Data
US 2020/0161704 A1    May 21, 2020

(30) Foreign Application Priority Data

May 27, 2017 (CN) .......................... 201710393438.4

(51) Int. Cl.
| | |
|---|---|
| H01M 10/0567 | (2010.01) |
| C07D 407/04 | (2006.01) |
| C07F 7/18 | (2006.01) |
| H01M 10/0525 | (2010.01) |
| H01M 10/0569 | (2010.01) |

(52) U.S. Cl.
CPC ...... *H01M 10/0567* (2013.01); *C07D 407/04* (2013.01); *C07F 7/1804* (2013.01); *H01M 10/0525* (2013.01); *H01M 10/0569* (2013.01); *H01M 2300/0025* (2013.01)

(58) Field of Classification Search
CPC .......... H01M 10/0567; H01M 10/0569; C07D 407/04
See application file for complete search history.

(56) References Cited

U.S. PATENT DOCUMENTS

| | | |
|---|---|---|
| 3,663,569 A | 5/1972 | Lew |
| 6,174,629 B1 | 1/2001 | Gan et al. |

(Continued)

FOREIGN PATENT DOCUMENTS

| | | |
|---|---|---|
| CN | 1495959 A | 5/2004 |
| CN | 102195076 A | 9/2011 |

(Continued)

OTHER PUBLICATIONS

Translation of written opinion (no date).*
Translation of JP 2006-219406 (no date).*
Translation of CN 105633461 (no date).*
International Search Report of PCT Patent Application No. PCT/CN2017/089664 dated Feb. 26, 2018.
Libo Hu et al., Fluorinated electrolytes for 5-V Li-ion chemistry: Dramatic enhancement of LiNi0.5Mn1.5O4/graphite cell performance by a lithium reservoir, Electrochemistry Communications, Apr. 2014, vol. 44, pp. 34-37.

*Primary Examiner* — Amanda C. Walke

(57) ABSTRACT

To solve the problems that the existing non-aqueous electrolyte for lithium ion battery containing fluorinated solvent generates serious gas expansion when improving high-temperature cycle performance and affects high-temperature safety performance of battery. The application provides a non-aqueous electrolyte for lithium ion battery. The non-aqueous electrolyte for lithium ion battery comprises a compound A and a compound B, wherein the compound A is at least one of compounds represented by the following structural formula I, formula II and formula III; the compound B is a compound represented by the following structural formula IV; formula I: $R_1$—COO—$R_2$; formula II: $R_3$—OCOO—$R_4$. The non-aqueous electrolyte for lithium ion battery provided by the invention contains both the compound A and the compound B, the synergistic effect of compound A and compound B can effectively improve high-temperature cycle performance and high-temperature storage performance of battery, and can also give consideration to low-temperature performance of battery.

Formula III

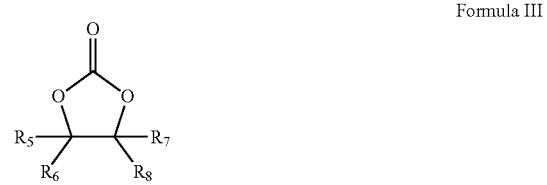

Formula IV

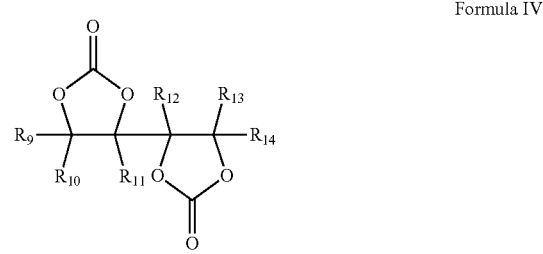

20 Claims, No Drawings

(56) References Cited

U.S. PATENT DOCUMENTS

| | | | |
|---|---|---|---|
| 9,608,289 B2* | 3/2017 | Ihara | H01M 10/052 |
| 9,847,524 B2* | 12/2017 | Yamamoto | H01M 4/0447 |
| 11,177,506 B2* | 11/2021 | Shi | H01M 10/052 |
| 2008/0248397 A1* | 10/2008 | Jung | H01M 10/0567 |
| | | | 429/314 |
| 2011/0159382 A1* | 6/2011 | Matsui | H01M 10/0569 |
| | | | 429/338 |
| 2015/0093653 A1* | 4/2015 | Coowar | H01M 4/386 |
| | | | 429/338 |
| 2015/0118576 A1* | 4/2015 | Chiga | H01M 10/052 |
| | | | 429/331 |
| 2017/0244096 A1* | 8/2017 | Kuzushima | H01M 4/0404 |
| 2019/0115623 A1* | 4/2019 | Ihara | H01M 10/625 |
| 2020/0020983 A1* | 1/2020 | Shi | H01M 10/0525 |
| 2020/0313237 A1* | 10/2020 | Hu | H01M 10/0525 |

FOREIGN PATENT DOCUMENTS

| | | |
|---|---|---|
| CN | 103151559 A | 6/2013 |
| CN | 103354962 A | 10/2013 |
| CN | 103441304 A | 12/2013 |
| CN | 103460496 A | 12/2013 |
| CN | 103594729 A | 2/2014 |
| CN | 104300174 A | 1/2015 |
| CN | 105051965 A | 11/2015 |
| CN | 105161763 A | 12/2015 |
| CN | 105580189 A | 5/2016 |
| CN | 105633461 A | 6/2016 |
| CN | 105830270 A | 8/2016 |
| CN | 106058317 A | 10/2016 |
| CN | 106252639 A | 12/2016 |
| CN | 106328996 A | 1/2017 |
| CN | 106410272 A | 2/2017 |
| GB | 1147540 A | 4/1969 |
| JP | 2000260467 A | 9/2000 |
| JP | 2006219406 A | 8/2006 |
| JP | 2014182951 A | 9/2014 |
| JP | 2014525667 A | 9/2014 |
| JP | 2015092476 A | 5/2015 |
| WO | 2016025589 A1 | 2/2016 |
| WO | 2016151983 A1 | 9/2016 |

* cited by examiner

NON-AQUEOUS ELECTROLYTE FOR LITHIUM ION BATTERY AND LITHIUM ION BATTERY

TECHNICAL FIELD

The invention relates to the field of lithium ion batteries, more particularly, to a non-aqueous electrolyte for lithium ion battery and lithium ion battery.

BACKGROUND

With the development of new energy vehicles and power energy storage, people have higher requirements for the performances of power lithium ion batteries, which requires further development of lithium ion batteries, so as to better meet the demand. Increasing the working voltage of battery is an effective method to improve the energy density of battery, but at the same time, the increasing of the working voltage of battery tends to degrade the performances of battery. This is because the existing common commercial electrolyte (such as carbonate electrolyte) will undergo oxidative decomposition when working at a voltage of 4.5-5V. On the one hand, some oxidation products of the electrolyte will deposit on the electrode surface, increasing the impedance of the battery and seriously deteriorating the electrochemical performance of the battery. On the other hand, the gas generated by the oxidative decomposition of electrolyte will cause the battery to swell, causing hidden trouble of safety.

In order to improve the stability of carbonate electrolyte under high voltage (4.5~5V), a practical method is to add fluorinated solvent to this kind of electrolyte to inhibit the electrolyte from decomposing too fast under high voltage condition. According to a literature report (Electrochemistry Communications 44 (2014) 34-37), fluorocarbonates can significantly improve the high-temperature cycle performance of high-voltage lithium ion batteries. However, repeated tests and studies by researchers in this field have found that batteries using fluorocarbonates alone generate serious gas when stored at high temperature, which has potential safety hazards. And, International Patent Publication No. WO2016/025589 discloses that adding fluorocarboxylic acid ester as electrolyte solvent to improve the high-temperature cycle performance of high-voltage lithium ion batteries. However, while fluorocarboxylic acid ester improves the cycle performance of the battery, there are problems in compatibility between fluorocarboxylic acid ester and carbon cathode material, which will cause the battery to inflate during high temperature cycle, bring potential safety hazards and deteriorate the battery performance.

SUMMARY

The application provides a non-aqueous electrolyte for lithium ion battery with good high-temperature cycle performance and less gas generation in high-temperature storage, aims to solve the problems that the existing non-aqueous electrolyte for lithium ion battery containing fluorinated solvent generates serious gas expansion when improving the high-temperature cycle performance and affects the high-temperature safety performance of the battery.

The application aims to provide a lithium ion battery containing the above-mentioned non-aqueous electrolyte for lithium ion battery.

The invention is realized as the following: a non-aqueous electrolyte for lithium ion battery, comprising a compound A and a compound B, wherein the compound A is at least one of compounds represented by the following structural formula I, formula II and formula III; the compound B is a compound represented by the following structural formula IV,

    ;formula I:

    ;formula II:

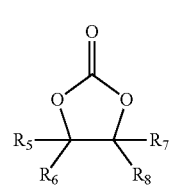

Formula III

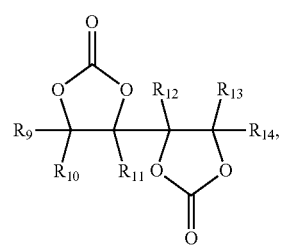

Formula IV in formula I, $R_1$ is a hydrogen atom, a C1-C5 hydrocarbon group or a C1-C5 fluorohydrocarbon group, $R_2$ is a C1-C5 hydrocarbon group or a C1-C5 fluorohydrocarbon group, and at least one of $R_1$ and $R_2$ contains a fluorine atom;

in formula II, $R_3$ and $R_4$ are each independently selected from C1-C5 hydrocarbon group or C1-C5 fluorohydrocarbon group, and at least one of $R_3$ and $R_4$ contains a fluorine atom;

in formula III, $R_5$, $R_6$, $R_7$ and $R_8$ are each independently selected from hydrogen atom, fluorine atom, C1-C4 hydrocarbon group or C1-C4 fluorohydrocarbon group, and at least one of $R_5$, $R_6$, $R_7$ and $R_8$ contains a fluorine atom;

in formula IV, $R_9$, $R_{10}$, $R_{11}$, $R_{12}$, $R_{13}$ and $R_{14}$ are each independently selected from one of hydrogen atom, fluorine atom or C1-C5 group.

Preferably, in formula IV, the C1-C5 group is selected from a hydrocarbon group, fluorinated hydrocarbon group, oxygen-containing hydrocarbon group, silicon-containing hydrocarbon group, and cyano-substituted hydrocarbon group.

Preferably, $R_9$, $R_{10}$, $R_{11}$, $R_{12}$, $R_{13}$ and $R_{14}$ are each independently selected from a hydrogen atom, fluorine atom, methyl group, ethyl group, methoxyl group, ethyoxyl group, trimethylsiloxy group, cyano group or trifluoromethyl group.

Preferably, the compound B comprises one or more of compounds 1-9 represented by the following structural formulae, Compound 1

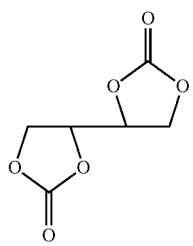

Compound 2

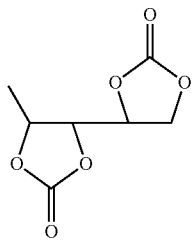

Compound 3

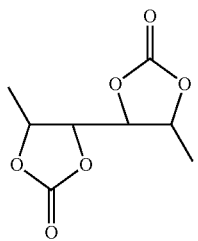

Compound 4

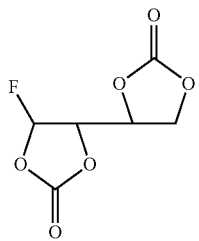

Compound 5

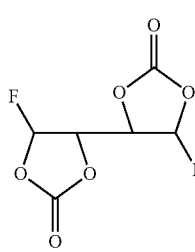

Compound 6

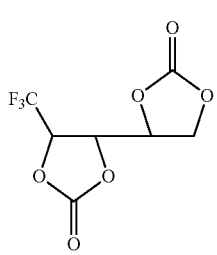

Compound 7

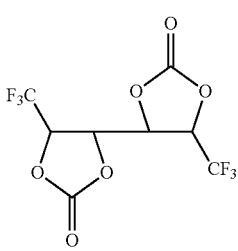

Compound 8

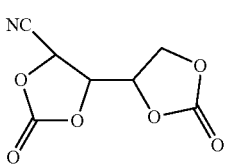

Compound 9

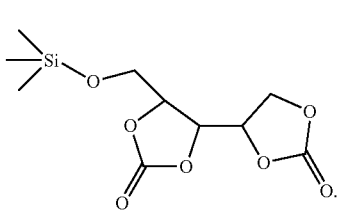

Preferably, the percentage mass content of the compound B is 0.1-5% based on the total mass of the non-aqueous electrolyte for lithium ion battery being 100%.

Preferably, the compound represented by formula I is selected from one or more of $H_3CCOOCH_2CF_2H$, $H_3CH_2CCOOCH_2CF_2H$, $HF_2CH_2CCOOCH_3$, $HF_2CH_2CCOOCH_2CH_3$, $HF_2CH_2CH_2CCOOCH_2CH_3$, $H_3CCOOCH_2CH_2CF_2H$, $H_3CH_2CCOOCH_2CH_2CF_2H$, $CH_3COOCH_2CF_3$, $HCOOCH_2CHF_2$, $HCOOCH_2CF_3$ and $CH_3COOCH_2CF_2CF_2H$.

Preferably, the compound represented by formula II is selected from one or more of $CH_3OCOOCH_2CF_2H$, $CH_3OCOOCH_2CF_3$, $CH_3OCOOCH_2CF_2CF_2H$, $HCF_2CH_2OCOOCH_2CH_3$ and $CF_3CH_2OCOOCH_2CH_3$.

Preferably, the compound represented by formula III is selected from one or more of compounds 10-13 represented by the following structures, Compound 10

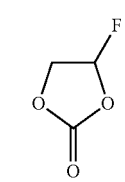

Compound 11

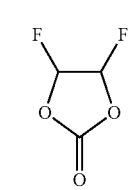

-continued

Compound 12

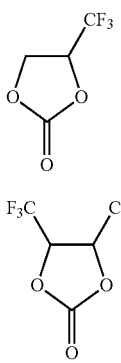

Compound 13

Preferably, the percentage mass content of the compound A is less than 80% based on the total mass of the non-aqueous electrolyte for lithium ion battery being 100%.

Preferably, the percentage mass content of the compound A is greater than 5% and less than or equal to 80% based on the total mass of the non-aqueous electrolyte for lithium ion battery being 100%.

Preferably, the compound A is at least one of compounds represented by structural formula I, formula II and formula III, and $R_5$ in formula III is fluorine, $R_6$, $R_7$ and $R_8$ are each independently selected from hydrogen atom, fluorine atom, C1-C4 hydrocarbon group or C1-C4 fluorohydrocarbon group, and $R_6$, $R_7$ and $R_8$ cannot be hydrogen atom at the same time; or $R_5$ is C1-C4 fluorine-containing hydrocarbon group, $R_6$, $R_7$ and $R_8$ are independently selected from hydrogen atom, fluorine atom, C1-C4 hydrocarbon group or C1-C4 fluorine-containing hydrocarbon group.

Preferably, the compound A is fluoroethylene carbonate, and the percentage mass content of the compound A is greater than 5% and less than or equal to 80% based on the total mass of the non-aqueous electrolyte of the lithium ion battery being 100%.

Preferably, the percentage mass content of the compound A is 10-80%, based on the total mass of the non-aqueous electrolyte of the lithium ion battery being 100%.

Preferably, the non-aqueous electrolyte for lithium ion battery comprises a solvent, and the solvent is selected from at least one of vinyl carbonate, propylene carbonate, butylene carbonate, dimethyl carbonate, diethyl carbonate, methyl ethyl carbonate and methyl propyl carbonate.

Preferably, the lithium ion non-aqueous electrolyte further comprises at least one of unsaturated cyclic carbonate compounds and sultone compounds.

More preferably, the unsaturated cyclic carbonate compound includes at least one of vinylene carbonate (VC) and vinyl ethylene carbonate (VEC).

More preferably, the sultone compound is selected from at least one of 1,3-propane sultone (PS), 1,4-butane sultone (BS), and 1,3-propene sultone (PST).

Preferably, the percentage mass content of the unsaturated cyclic carbonate compound is 0.1-5% based on the total mass of the non-aqueous electrolyte of the lithium ion battery being 100%; the percentage mass content of the sultone compound is 0.1-5% based on the total mass of the non-aqueous electrolyte of the lithium ion battery being 100%

Preferably, the non-aqueous electrolyte for lithium ion battery comprises lithium salt; the lithium salt can be selected from one or more of $LiPF_6$, LiBOB and $LiBF_4$.

Preferably, the lithium salt content in the non-aqueous electrolyte for lithium ion battery is 0.1-15%.

The non-aqueous electrolyte for lithium ion battery comprises a solvent, and the solvent is selected from at least one of vinyl carbonate, propylene carbonate, butylene carbonate, dimethyl carbonate, diethyl carbonate, methyl ethyl carbonate and methyl propyl carbonate.

And, a lithium ion battery, comprises a positive electrode, a negative electrode, a separator interposed between the positive electrode and the negative electrode, and an electrolyte, wherein the electrolyte is the non-aqueous electrolyte for lithium ion battery.

Preferably, the positive electrode comprises a positive electrode active material, and the positive electrode active material is at least one of $LiNi_xCo_yMn_zL_{(1-x-y-z)}O_2$, $LiCo_{x'}L_{(1-x')}O_2$, $LiNi_{x''}L'_{y'}Mn_{(2-x''-y')}O_4$ and $Li_xMPO_4$, wherein, L is at least one of Al, Sr, Mg, Ti, Ca, Zr, Zn, Si or Fe, 0≤x≤1, 0≤y≤1, 0≤z≤1, 0<x+y+z≤1, 0<x'≤1, 0.3≤x"≤0.6, 0.01≤y'≤0.2, L' is at least one of Co, Al, Sr, Mg, Ti, Ca, Zr, Zn, Si and Fe; 0.5≤z'≤1, M is at least one of Fe, Mn and Co.

The non-aqueous electrolyte for lithium ion battery provided by the invention contains both the compound A and the compound B, the synergistic effect of compound A and compound B can ensure the thermal stability (high-temperature safety performance) of the negative electrode passivation film, and effectively improve the high-temperature cycle performance and the high-temperature storage performance of battery, and can also give consideration to the low-temperature performance of battery. The lithium ion battery containing the non-aqueous electrolyte has excellent high-temperature cycle performance, high-temperature storage performance and good low-temperature performance The lithium ion battery provided by the embodiments of the invention contains the non-aqueous electrolyte, so that the lithium ion battery has better high-temperature cycle performance, high-temperature storage performance and low-temperature performance.

DETAILED DESCRIPTION OF DISCLOSED EMBODIMENT

In order to make the technical problems to be solved, technical solutions and beneficial effects more apparent and clearer, the present application will be described in further detail below with reference to embodiments. It should be understood that the specific embodiments described herein are only for the purpose of explaining the present invention and are not intended to limit the present invention.

In the embodiments of the invention, the names and their English abbreviations are as follows:
FEC: fluoroethylene carbonate;
DFEC: 1,2-difluoroethylene carbonate;
PC: propylene carbonate;
EC: ethylene carbonate;
DEC: diethyl carbonate.

The embodiment of the invention provides a non-aqueous electrolyte for lithium ion battery, comprising a compound A and a compound B, wherein the compound A is at least one of compounds represented by the following structural formula I, formula II and formula III; the compound B is a compound represented by the following structural formula IV, $R_1$—COO—$R_2$   ;formula I:

$R_3$—OCOO—$R_4$   ;formula II:

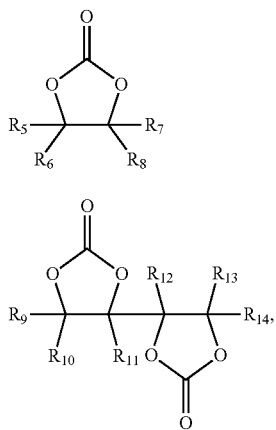

Formula III

Formula IV

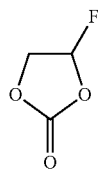

Compound 10

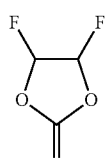

Compound 11

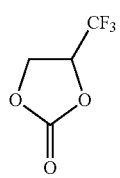

Compound 12

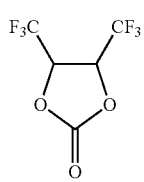

Compound 13 in formula I, $R_1$ is a hydrogen atom, a C1-C5 hydrocarbon group or a C1-C5 fluorohydrocarbon group, $R_2$ is a C1-C5 hydrocarbon group or a C1-C5 fluorohydrocarbon group, and at least one of $R_1$ and $R_2$ contains a fluorine atom;

in formula II, $R_3$ and $R_4$ are each independently selected from C1-C5 hydrocarbon group or C1-C5 fluorohydrocarbon group, and at least one of $R_3$ and $R_4$ contains a fluorine atom;

in formula III, $R_5$, $R_6$, $R_7$ and $R_8$ are each independently selected from hydrogen atom, fluorine atom, C1-C4 hydrocarbon group or C1-C4 fluorohydrocarbon group, and at least one of $R_5$, $R_6$, $R_7$ and $R_8$ contains a fluorine atom;

in formula IV, $R_9$, $R_{10}$, $R_{11}$, $R_{12}$, $R_{13}$ and $R_{14}$ are each independently selected from one of hydrogen atom, fluorine atom or C1-C5 group.

In the embodiment of the invention, C1-C5 refers to the number of carbon atoms being 1-5, similarly, C1-C4 refers to the number of carbon atoms being 1-4.

Preferably, the compound represented by formula I is selected from one or more of $H_3CCOOCH_2CF_2H$, $H_3CH_2CCOOCH_2CF_2H$, $HF_2CH_2CCOOCH_3$, $HF_2CH_2CCOOCH_2CH_3$, $HF_2CH_2CH_2CCOOCH_2CH_3$, $H_3CCOOCH_2CH_2CF_2H$, $H_3CH_2CCOOCH_2CH_2CF_2H$, $CH_3COOCH_2CF_3$, $HCOOCH_2CHF_2$, $HCOOCH_2CF_3$ and $CH_3COOCH_2CF_2H$, but is not limited thereto.

Preferably, the compound represented by formula II is selected from one or more of $CH_3OCOOCH_2CF_2H$, $CH_3OCOOCH_2CF_3$ (methyl 2,2,2-trifluoroethyl carbonate), $CH_3OCOOCH_2CF_2CF_2H$, $HCF_2CH_2OCOOCH_2CH_3$ and $CF_3CH_2OCOOCH_2CH_3$, but is not limited thereto.

in formula III, $R_5$, $R_6$, $R_7$ and $R_8$ are each independently selected from hydrogen atom, fluorine atom, C1-C4 hydrocarbon group or C1-C4 fluorohydrocarbon group, and at least one of $R_5$, $R_6$, $R_7$ and $R_8$ contains a fluorine atom;

Specifically, the compound represented by formula III can be fluoroethylene carbonate, or $R_5$ in formula III is fluorine, $R_6$, $R_7$ and $R_8$ are each independently selected from hydrogen atom, fluorine atom, C1-C4 hydrocarbon group or C1-C4 fluorohydrocarbon group, and $R_6$, $R_7$ and $R_8$ cannot be hydrogen atom at the same time; or $R_5$ is C1-C4 fluorine-containing hydrocarbon group, $R_6$, $R_7$ and $R_8$ are independently selected from hydrogen atom, fluorine atom, C1-C4 hydrocarbon group or C1-C4 fluorine-containing hydrocarbon group.

Preferably, the compound represented by formula III is selected from one or more of compounds 10-13 represented by the following structures, and is not limited thereto.

The above preferred structures of formula I, formula II and formula III have better effect of improving the oxidation decomposition potential of the electrolyte, and cooperate with the compound B more effectively to improve the high-temperature cycle performance and high-temperature storage performance of the electrolyte, meanwhile, can also give consideration to the low-temperature performance of the battery.

The content of the above compound A can be varied within a wide range. Preferably, based on the total mass of the non-aqueous electrolyte for lithium ion battery being 100%, the percentage mass content of the compound A is less than 80%, for example, it may be 1%, 2%, 5%, 6%, 8%, 10%, 15%, 20%, 30%, 40%, 50%, 60%, 70%, 80%. More preferably, the percentage mass content of the compound A is greater than 5% and less than or equal to 80%, more preferably, the percentage mass content of the compound A is 10-80%.

When compound A is the compound represented by formula III, and is not FEC (i.e., $R_5$ in the formula III is fluorine, $R_6$, $R_7$ and $R_8$ are each independently selected from hydrogen atom, fluorine atom, C1-C4 hydrocarbon group or C1-C4 fluorohydrocarbon group, and $R_6$, $R_7$ and $R_8$ cannot be hydrogen atom at the same time; Or $R_5$ is a C1-C4 fluoroalkyl group, $R_6$, $R_7$ and $R_8$ are independently selected from hydrogen atom, fluorine atom, C1-C4 hydrocarbyl group, or C1-C4 fluoroalkyl group), the content thereof can be varied within a wide range without any particular limitation. Preferably, based on the total mass of the non-aqueous electrolyte for lithium ion battery being 100%, the percentage mass content of the compound A is less than 80%; for example, it may be 1%, 2%, 5%, 6%, 8%, 10%, 15%, 20%, 30%, 40%, 50%, 60%, 70%, 80%. More preferably, the percentage mass content of the compound A is greater than 5% and less than or equal to 80%, more preferably, the percentage mass content of the compound A is 10-80%.

When the compound A is FEC, the percentage mass content of the compound A is greater than 5% and less than or equal to 80% based on the total mass of the non-aqueous electrolyte for lithium ion battery being 100%.

It is understood that if the non-aqueous electrolyte for lithium ion battery contains one of the above substances, the content is the content of the one substance; If the non-aqueous electrolyte for lithium ion battery contains a plurality of the above substances, the content is the sum of the contents of the plurality of substances.

The non-aqueous electrolyte for lithium ion battery provided by the embodiments of the invention contains a compound A (fluorinated solvent), and the compound A has better oxidation resistance than carbonate and can improve the oxidation decomposition potential of the electrolyte. In addition, the compound A (fluorocarbonate and fluorocarboxylate) can form a passivation film on the surface of the negative electrode and inhibit the decomposition reaction of the electrolyte. However, under the condition of high voltage (4.5-5V), the compound A produces serious gas when the battery is formed, stored at high temperature and cycled at high temperature, which deteriorates the battery performances and brings potential safety hazards.

Specifically, in the high-temperature storage process of the battery, the thermal stability of the passivation film of the fluorocarbonate solvent represented by formula II and formula III is not ideal, a large amount of gas is generated, and the high-temperature storage performance of the battery is reduced. During the initial charge process of the battery, the fluorocarboxylic acid ester solvent represented by the formula I decomposes on the surface of the negative electrode and generates a large amount of gas, which leads to poor contact between electrode plates, thereby reducing the performances of the lithium ion battery.

In the embodiments of the invention, the compound B represented by the structural formula IV is added to the non-aqueous electrolyte of the lithium ion battery on the basis of the compound A, the two compounds works together to improve the high-temperature storage performance, high-temperature cycle performance and low-temperature performance of the lithium ion battery. Specifically, the compound B forms a dense passivation film on the negative electrode in the battery formation process, preventing the decomposition of fluorinated solvent molecules (the compound A), inhibiting the generation of gas by the fluorinated solvent, which can improve the thermal stability of the negative electrode passivation film, effectively enhance the high-temperature cycle performance and high-temperature storage performance of the battery, hence ensuring the high-temperature performance of the lithium ion battery. At the same time, the passivation film formed by decomposition of the compound B has lower impedance and less influence on impedance growth, so that the low-temperature performance of the lithium ion battery can also be considered. In the embodiments of the invention, the compound A and the compound B are used together, because when the compound A is subjected to the film forming reaction on the surface of the negative electrode, the compound B also participates in the film forming reactions of positive and negative electrodes, so that the passivation layer components of positive and negative electrodes comprise both the decomposition products of the compound A and the compound B, thereby effectively improving the interface conditions of the positive and negative electrodes. The synergistic effect of the two compounds use together is better than that of the simple addition of the two compounds used separately.

In the compound B, the C1-C5 group is selected from a hydrocarbon group, fluorinated hydrocarbon group, oxygen-containing hydrocarbon group, silicon-containing hydrocarbon group, and cyano-substituted hydrocarbon group. In the compound B, $R_9$, $R_{10}$, $R_{11}$, $R_{12}$, $R_{13}$ and $R_{14}$ are each independently selected from a hydrogen atom, fluorine atom, methyl group, ethyl group, methoxyl group, ethyoxyl group, trimethylsiloxy group, cyano group or trifluoromethyl group.

Preferably, the compound B comprises one or more of compounds 1-9 represented by the following structural formulae,

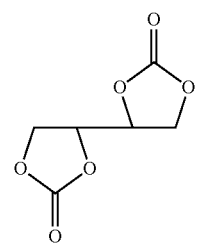

Compound 1

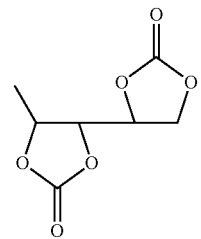

Compound 2

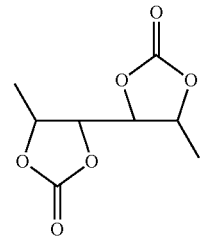

Compound 3

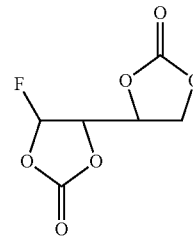

Compound 4

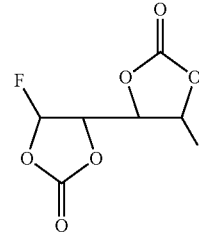

Compound 5

-continued

Compound 6
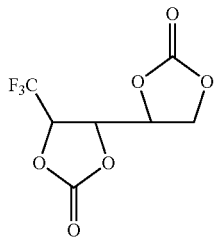

Compound 7
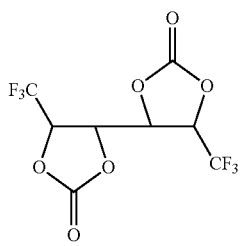

Compound 8
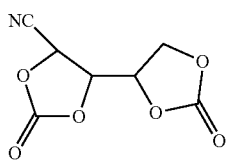

Compound 9
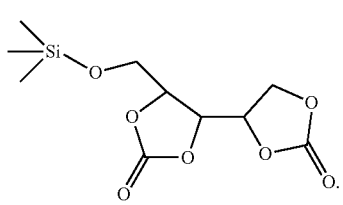

The preferred compound B can better cooperate with the compound A to endow the lithium ion battery with better comprehensive performances (high-temperature cycle performance, high-temperature storage performance and low-temperature performance).

The synthesis method of the compound B presented by formula IV is conventional, for example, the compound B can be prepared by ester exchange reaction between polyol (such as erythritol, xylitol, etc.) and carbonate (such as dimethyl carbonate, diethyl carbonate, vinyl carbonate, etc.) in the presence of basic catalyst. An example of the synthetic route is as follows:

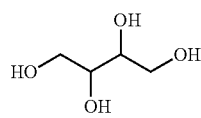 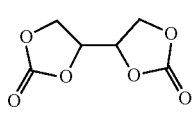

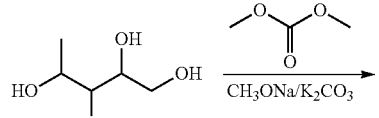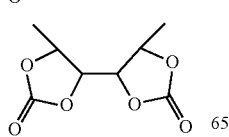

The fluorine-containing compound in compound B is prepared by: fluorinating the corresponding carbonate and mixture $F_2/N_2$, and then recrystallizing or purifying by column chromatography. An example of the synthetic route is as follows:

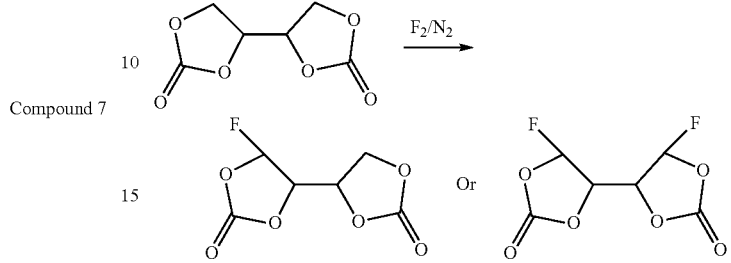

The cyano group-containing compound in compound B is prepared by: the chlorination reaction of the corresponding carbonate and sulfonyl chloride, then reacting with NaCN or KCN, and then recrystallizing or purifying by column chromatography. An example of the synthetic route is as follows:

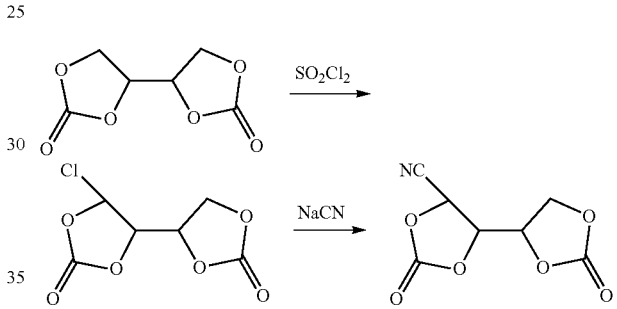

The trimethylsilanolate-containing compound in the compound B is prepared by: the substitution reaction of the corresponding hydroxy carbonate and silazane, then ecrystallizing or purifying by column chromatography. An example of the synthetic route is as follows:

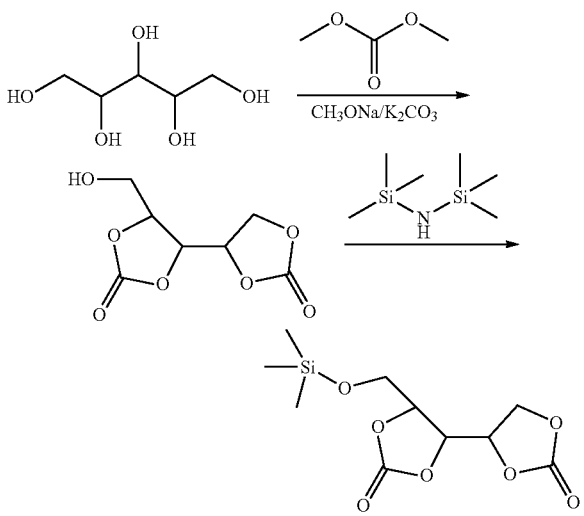

Preferably, the percentage mass content of the compound B is 0.1-5% based on the total mass of the non-aqueous electrolyte for lithium ion battery being 100%. For example, the percentage mass content of the compound B may be 0.1%, 0.2%, 0.4%, 0.5%, 0.6%, 0.8%, 1%, 1.2%, 1.5%, 1.8%, 2%, 2.5%, 3%, 3.5%, 4%, 4.5%, 5%. When the percentage mass content of the compound B is less than 0.1%, it is not conductive for the film formation at the negative electrode, and the effect of improving cycle performance is reduced; when the percentage mass content of the compound B is more than 5%, it is not conducive to uniform dissolution in the electrolyte, and the film formation at the electrode interface is quite thick, which will increase the battery impedance and deteriorate the battery performance.

Based on the above embodiments, it is preferred that the lithium ion non-aqueous electrolyte further comprises at least one of unsaturated cyclic carbonate compounds and sultone compounds.

Preferably, the unsaturated cyclic carbonate compound includes at least one of vinylene carbonate (VC) and vinyl ethylene carbonate (VEC). The sultone compound is selected from at least one of 1,3-propane sultone (PS), 1,4-butane sultone (BS), and 1,3-propene sultone (PST).

The content of unsaturated cyclic carbonate compound is 0.1-5% based on the total mass of the non-aqueous electrolyte for lithium ion battery being 100%.

The percentage mass content of sultone compound is 0.1-5% based on the total mass of the non-aqueous electrolyte for lithium ion battery being 100%.

The lithium ion non-aqueous electrolyte comprises lithium salt, and the lithium salt is not particularly limited in the present invention, various existing lithium salts can be used, for example, the lithium salt can be selected from one or more of $LiPF_6$, LiBOB and $LiBF_4$. The content of the lithium salt can vary within a wide range, and preferably, the content of the lithium salt in the non-aqueous electrolyte of the lithium ion battery is 0.1-15%.

Preferably, the non-aqueous electrolyte for lithium ion battery further comprises at least one of vinyl carbonate, propylene carbonate, butylene carbonate, dimethyl carbonate, diethyl carbonate, methyl ethyl carbonate and methyl propyl carbonate.

The non-aqueous electrolyte for lithium ion battery provided by the embodiments of the invention contains both the compound A and the compound B, the synergistic effect of compound A and compound B can ensure the thermal stability (high-temperature safety performance) of the negative electrode passivation film, and effectively improve the high-temperature cycle performance and the high-temperature storage performance of battery, and can also give consideration to the low-temperature performance of battery. The lithium ion battery containing the non-aqueous electrolyte has excellent high-temperature cycle performance, high-temperature storage performance and good low-temperature performance.

And, the embodiment of the invention also provides a lithium ion battery, comprising a positive electrode, a negative electrode, a separator interposed between the positive electrode and the negative electrode, and an electrolyte, wherein the electrolyte is the non-aqueous electrolyte for lithium ion battery.

Preferably, the positive electrode comprises a positive electrode active material, and the positive electrode active material is at least one of $LiNi_xCo_yMn_zL_{(1-x-y-z)}O_2$, $LiCo_{x'}L_{(1-x')}O_2$, $LiNi_{x''}L'_yMn_{(2-x-41-y')}O_4$, $Li_z$ and $MPO_4$, wherein, L is at least one of Al, Sr, Mg, Ti, Ca, Zr, Zn, Si or Fe, 0≤x≤1, 0≤y≤1, 0≤z≤1, 0<x+y+z≤1, 0<x'≤1, 0.3≤x"≤0.6, 0.01≤y'≤0.2, L' is at least one of Co, Al, Sr, Mg, Ti, Ca, Zr, Zn, Si and Fe; 0.5≤z'≤1, M is at least one of Fe, Mn and Co.

In the embodiment of the present invention, the positive electrode, negative electrode and the separator are not specifically limited, they can be the conventional ones in the art.

The lithium ion battery provided by the embodiments of the invention contains the non-aqueous electrolyte, so that the lithium ion battery has better high-temperature cycle performance, high-temperature storage performance and low-temperature performance The following description will be made with reference to specific embodiments.

Embodiment 1

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 1, based on the total weight of the non-aqueous electrolyte taken as 100% by weight, and conventional lithium salts without showing.

Embodiment 2

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 2, based on the total weight of the non-aqueous electrolyte taken as 100% by weight, and conventional lithium salts without showing.

Embodiment 3

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 3, based on the total weight of the non-aqueous electrolyte taken as 100% by weight, and conventional lithium salts without showing.

Embodiment 4

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 4, based on the total weight of the non-aqueous electrolyte taken as 100% by weight, and conventional lithium salts without showing.

Embodiment 5

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 5, based on the total weight of the non-aqueous electrolyte taken as 100% by weight, and conventional lithium salts without showing.

Embodiment 6

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 6, based on the total weight of the non-aqueous electrolyte taken as 100% by weight, and conventional lithium salts without showing.

Embodiment 7

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 7, based on the total weight of the non-aqueous electrolyte taken as 100% by weight, and conventional lithium salts without showing.

Embodiment 8

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 8, based on the total weight of the non-aqueous electrolyte taken as 100% by weight, and conventional lithium salts without showing.

Embodiment 9

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 9, based on the total weight of the non-aqueous electrolyte taken as 100% by weight, and conventional lithium salts without showing.

Embodiment 10

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 10, based on the total weight of the non-aqueous electrolyte taken as 100% by weight, and conventional lithium salts without showing.

Embodiment 11

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 11, based on the total weight of the non-aqueous electrolyte taken as 100% by weight, and conventional lithium salts without showing.

Embodiment 12

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 12, based on the total weight of the non-aqueous electrolyte taken as 100% by weight, and conventional lithium salts without showing.

Embodiment 13

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Embodiment 13, based on the total weight of the non-aqueous electrolyte taken as 100% by weight, and conventional lithium salts without showing.

Embodiment 14

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Embodiment 14, based on the total weight of the non-aqueous electrolyte taken as 100% by weight, and conventional lithium salts without showing.

Embodiment 15

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Embodiment 15, based on the total weight of the non-aqueous electrolyte taken as 100% by weight, and conventional lithium salts without showing.

Embodiment 16

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Embodiment 16, based on the total weight of the non-aqueous electrolyte taken as 100% by weight, and conventional lithium salts without showing.

Embodiment 17

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Embodiment 17, based on the total weight of the non-aqueous electrolyte taken as 100% by weight, and conventional lithium salts without showing.

Comparative Example 1

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 1, based on the total weight of the non-aqueous electrolyte taken as 100% by weight, and conventional lithium salts without showing.

Comparative Example 2

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 2, based on the total weight of the non-aqueous electrolyte taken as 100% by weight, and conventional lithium salts without showing.

Comparative Example 3

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 3, based on the total weight of the non-aqueous electrolyte taken as 100% by weight, and conventional lithium salts without showing.

Comparative Example 4

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 4, based on the total weight of the non-aqueous electrolyte taken as 100% by weight, and conventional lithium salts without showing.

Comparative Example 5

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 5, based on the total weight of the non-aqueous electrolyte taken as 100% by weight, and conventional lithium salts without showing.

Comparative Example 6

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 6, based on the total weight of the non-aqueous electrolyte taken as 100% by weight, and conventional lithium salts without showing.

Comparative Example 7

A 4.4V $LiNi_{0.5}Co_{0.2}Mn_{0.3}O_2$/artificial graphite battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 1 of Comparative Example 7, based on the total weight of the non-aqueous electrolyte taken as 100% by weight, and conventional lithium salts without showing.

Comparative Example 8

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Comparative Example 8, based on the total weight of the non-aqueous electrolyte taken as 100% by weight, and conventional lithium salts without showing.

Comparative Example 9

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Comparative Example 9, based on the total weight of the non-aqueous electrolyte taken as 100% by weight, and conventional lithium salts without showing.

Comparative Example 10

A 4.2V $LiNi_{0.8}Co_{0.15}Al_{0.05}O_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Comparative Example 10, based on the total weight of the non-aqueous electrolyte taken as 100% by weight, and conventional lithium salts without showing.

Comparative Example 11

A 4.2V LiNi$_{0.8}$Co$_{0.15}$Al$_{0.05}$O$_2$/Si—C battery, comprises a positive electrode, a negative electrode, a separator interposed between the positive electrode and the negative electrode, and an electrolyte, wherein the electrolyte is a non-aqueous electrolyte and comprises the following components in percentage by mass as shown in Table 3 of Comparative Example 11, based on the total weight of the non-aqueous electrolyte taken as 100% by weight, and conventional lithium salts without showing.

The Embodiments 1-13, Comparative Examples 1-7 (4.4V LiNi$_{0.5}$Co$_{0.2}$Mn$_{0.3}$O$_2$/artificial graphite battery), Embodiments 14-17, Comparative Examples 8-11 (4.2V LiNi$_{0.8}$Co$_{0.15}$Al$_{0.05}$O$_2$/Si—C battery) of the present invention were tested for performance, and the test parameters and test methods are as follows:

(1) High-temperature cycle performance is demonstrated by testing the capacity retention rate after Nth cycles at 1C rate, 45V. The specific method is as follows: at 45V, the formed battery was charged with 1C constant current/constant voltage to 4.4V (LiNi$_{0.5}$Co$_{0.2}$Mn$_{0.3}$O$_2$/artificial graphite battery)/4.2V (LiNi$_{0.8}$Co$_{0.15}$Al$_{0.05}$O$_2$/Si—C battery), the cutoff current was 0.01C, and then discharged to 3.0V with 1C constant current. After such charging/discharging for N cycles, the capacity retention after the Nth cycle was calculated to evaluate its high-temperature cycle performance.

The calculation formula of the Nth cycle capacity retention rate at 45V 1C is as follows:

The Nth cycle capacity retention rate (%)=(the Nth cycle discharge capacity/the first cycle discharge capacity)*100%;

(2) Test method for capacity retention rate, capacity recovery rate and thickness expansion rate after 30 days of storage at 60° C.: the formed battery was charged to 4.4V (LiNi$_{0.5}$Co$_{0.2}$Mn$_{0.3}$O$_2$/artificial graphite battery)/4.2V (LiNi$_{0.8}$Co$_{0.15}$Al$_{0.005}$O$_2$/Si—C battery) at room temperature with 1C constant current/constant voltage, the cutoff current was 0.01 C, then discharged to 3.0V with 1C constant current, the initial discharge capacity of the battery was measured, then charged to 4.4V with 1C constant current/constant voltage, the cutoff current was 0.01C, and the initial thickness of the battery was measured. Then the battery was stored at 60° C. for 30 days, measured the thickness of the battery, discharged it to 3.0V with 1C constant current, measured the capacity retention of the battery, then charged it to the operating voltage with 1C constant current/constant voltage, the cutoff current was 0.01C, then discharged it to 3.0V with 1C constant current, then measured the recovery capacity. The calculation formulas for capacity retention rate and capacity recovery rate are as follows:

Battery capacity retention rate (%)=(retention capacity/initial capacity)*100%;

Battery capacity recovery rate (%)=(recovery capacity/initial capacity)*100%;

Battery thickness expansion rate (%)=(thickness after 30 days−initial thickness)/initial thickness*100%.

(3) Low-temperature discharge performance: at 25V, the formed battery was charged to 4.4V with 1C constant current/constant voltage, then charged to drop the current to 0.01C with constant voltage, and then discharged to 3.0V with 1C constant current, the room temperature discharge capacity was recorded. Then charged to 4.4V with 1C constant current (LiNi$_{0.5}$Co$_{0.2}$Mn$_{0.3}$O$_2$/artificial graphite battery)/4.2V (LiNi$_{0.8}$Co$_{0.15}$Al$_{0.05}$O$_2$/silicon-carbon battery), then charged to drop the current to 0.01C with constant voltage, the battery was placed in an environment of −20° C. for 12 h, then discharge to 3.0V with 0.2 C constant current, the discharge capacity of −20° C. was recorded.

Discharge efficiency at low temperature of −20° C.=0.2 C discharge capacity (−20° C.)/1 C discharge capacity (25° C.)×100%.

TABLE 1

| | Total weight percentage, composition and weight ratio of the solvent | Additive and weight percentage |
|---|---|---|
| Embodiment 1 | Total weight percentage: 87% FEC/PC/DEC = 2/1/1 | Compound 1: 0.5% |
| Embodiment 2 | Total weight percentage: 85.5% FEC/PC/DEC = 2/1/1 | Compound 1: 2% |
| Embodiment 3 | Total weight percentage: 85.5% FEC/PC/DEC = 2/1/1 | Compound 2: 2% |
| Embodiment 4 | Total weight percentage: 83.5% FEC/PC/DEC = 2/1/1 | Compound 1: 4% |
| Embodiment 5 | Total weight percentage: 85.5% DFEA/PC/DEC/EC = 1/1/1/1 | Compound 1: 2% |
| Embodiment 6 | Total weight percentage: 85.5% DFEA/PC/DEC/EC = 1/1/1/1 | Compound 2: 2% |
| Embodiment 7 | Total weight percentage: 84.5% DFEA/PC/DEC/EC = 1/1/1/1 | Compound 1: 3% |
| Embodiment 8 | Total weight percentage: 85.5% FEC/PC/DFEA = 2/1/1 | Compound 1: 2% |
| Embodiment 9 | Total weight percentage: 84.5% FEC/PC/DFEA = 2/1/1 | Compound 1: 3% |
| Embodiment 10 | Total weight percentage: 85.5% FEC/PC/Methyl 2,2,2-trifluoroethyl carbonate = 2/1/1 | Compound 1: 2% |
| Embodiment 11 | Total weight percentage: 84.5% DFEA/PC/DEC/EC = 1/1/1/1 | Compound 1: 2% LiBOB: 1% |
| Embodiment 12 | Total weight percentage: 84.5% DFEA/PC/DEC/EC = 1/1/1/1 | Compound 1: 2% VC: 1% |
| Embodiment 13 | Total weight percentage: 84.5% DFEA/PC/DEC/EC = 1/1/1/1 | Compound 1: 2% PS: 1% |
| Comparative example 1 | Total weight percentage: 87.5% FEC/PC/DEC = 2/1/1 | |
| Comparative example 2 | Total weight percentage: 87.5% DFEA/PC/DEC/EC = 1/1/1/1 | |
| Comparative example 3 | Total weight percentage: 87.5% FEC/PC/DFEA = 2/1/1 | |
| Comparative example 4 | Total weight percentage: 87.5% FEC/PC/Methyl 2,2,2-trifluoroethyl carbonate = 2/1/1 | |
| Comparative example 5 | Total weight percentage: 86.5% FEC/PC/DEC = 2/1/1 | LiBOB: 1% |
| Comparative example 6 | Total weight percentage: 86.5% DFEA/PC/DEC/EC = 1/1/1/1 | VC: 1% |
| Comparative example 7 | Total weight percentage: 86.5% DFEA/PC/DEC/EC = 1/1/1/1 | PS: 1% |

The test results of Embodiments 1-13 and Comparative examples 1-7 are shown in Table 2 below.

TABLE 2

| | The 400th cycle capacity retention rate at 45° C. | After 30 days of storage at high temperature of 60° C. | | | 0.2 C |
|---|---|---|---|---|---|
| | | Capacity retention rate | Capacity recovery rate | Thickness expansion rate | Discharge Efficiency (−20° C.) |
| Embodiment 1 | 65.3% | 70.2% | 75.9% | 44.3% | 75.3% |
| Embodiment 2 | 76.9% | 80.6% | 85.1% | 24.9% | 75.0% |

TABLE 2-continued

| | The 400th cycle capacity retention rate at 45° C. | After 30 days of storage at high temperature of 60° C. | | | 0.2 C Discharge Efficiency (−20° C.) |
| --- | --- | --- | --- | --- | --- |
| | | Capacity retention rate | Capacity recovery rate | Thickness expansion rate | |
| Embodiment 3 | 73.3% | 76.3% | 81.5% | 30.3% | 76.0% |
| Embodiment 4 | 85.1% | 85.4% | 90.5% | 17.8% | 75.6% |
| Embodiment 5 | 70.8% | 71.2% | 75.9% | 33.5% | 76.7% |
| Embodiment 6 | 68.5% | 68.3% | 74.1% | 34.6% | 74.2% |
| Embodiment 7 | 75.4% | 78.8% | 84.2% | 28.8% | 76.2% |
| Embodiment 8 | 76.9% | 78.4% | 84.1% | 20.4% | 76.0% |
| Embodiment 9 | 86.5% | 86.2% | 91.1% | 17.4% | 75.1% |
| Embodiment 10 | 73.2% | 77.7% | 83.2% | 30.5% | 73.8% |
| Embodiment 11 | 80.1% | 82.5% | 87.6% | 17.8% | 74.4% |
| Embodiment 12 | 78.5% | 79.3% | 84.2% | 30.1% | 73.7% |
| Embodiment 13 | 75.5% | 81.1% | 85.5% | 26.6% | 72.4% |
| Comparative example 1 | 51.4% | 45.5% | 52.1% | 52.4% | 75.1% |
| Comparative example 2 | 34.7% | 35.9% | 41.2% | 72.4% | 77.0% |
| Comparative example 3 | 54.5% | 51.5% | 55.3% | 65.4% | 75.3% |
| Comparative example 4 | 45.2% | 44.1% | 50.2% | 76.2% | 74.0% |
| Comparative example 5 | 65.4% | 63.5% | 66.6% | 48.5% | 71.4% |
| Comparative example 6 | 62.3% | 64.7% | 65.6% | 49.5% | 73.5% |
| Comparative example 7 | 55.8% | 66.5% | 66.6% | 50.5% | 72.2% |

Referring to Table 1, the Embodiments 1-4 and Comparative Example 1 are compared, in the lithium ion non-aqueous electrolyte of Embodiments 1-4 and Comparative Example 1, the additive composition and proportion of Compound A are the same (FEC/PC/DEC=2/1/1), however, the Comparative Example 1 was not added with Compound B, and Embodiments 1-4 were added with Compound B. The results showed that compared with Comparative Example 1 to which only compound A was added, the battery made of lithium ion non-aqueous electrolyte containing both compound A and compound B had obviously improved high-temperature cycle performance and high-temperature storage performance, reaching 85.1% (51.4% in Cited document 1) after 300 cycles at 45V. The capacity retention rate, capacity recovery rate and thickness expansion rate after 30 days of storage at high temperature of 60° C., reached 85.4% (45.5% in Cited document 1), 90.5% (52.1% in Cited document 1), 17.8% (52.4% in Cited document 1), respectively, and the 0.2C Discharge Efficiency (−20° C.) was 75.0-76%(75.1% in Cited document 1). It can be seen that the synergistic effect of the compound A and the compound B can obviously improve the high-temperature cycle performance and the high-temperature storage performance of the battery. Moreover, the combination of the compound A and the compound B has no obvious influence on the battery impedance, so that batteries made of the lithium ion non-aqueous electrolyte have better low-temperature performance Meanwhile, the compound B is in the range of 0.5-4%, and the higher the percentage mass content is, the better the high-temperature cycle performance and high-temperature storage performance are.

Comparing the Embodiments 5-7 and Comparative Example 2, in the lithium ion non-aqueous electrolyte of Embodiments 5-7 and Comparative Example 2, the additive composition and proportion of Compound A are the same (DFEA/PC/DEC/EC=1/1/1/1), however, Comparative Example 2 was not added with Compound B, and Embodiments 5-7 were added with Compound B. The results showed that compared with Comparative Example 2 to which only compound A was added, the battery made of lithium ion non-aqueous electrolyte containing both compound A and compound B had obviously improved high-temperature cycle performance and high-temperature storage performance, reaching 75.4% (34.7% in Cited document 2) after 400 cycles at 45V. The capacity retention rate, capacity recovery rate and thickness expansion rate after 30 days of storage at high temperature of 60° C., reached 78.8% (35.9% in Cited document 2), 84.2% (41.2% in Cited document 2), 28.8% (72.4% in Cited document 2), respectively, and the 0.2C Discharge Efficiency (−20° C.) was 74.2-76.7% (77% in Cited document 2). It can be seen that the synergistic effect of the compound A and the compound B can obviously improve the high-temperature cycle performance and the high-temperature storage performance of the battery. Meanwhile, the combination of the compound A and the compound B has no obvious influence on the battery impedance, so that batteries made of the lithium ion non-aqueous electrolyte have better low-temperature performance.

Comparing the Embodiments 8-9 and Comparative Example 3, in the lithium ion non-aqueous electrolyte of Embodiments 8-9 and Comparative Example 3, the additive composition and proportion of Compound A are the same (FEC/PC/DFEA=2/1/1, however, Comparative Example 3 was not added with Compound B, and Embodiments 8-9 were added with Compound B. The results showed that compared with Comparative Example 3 to which only compound A was added, the battery made of lithium ion non-aqueous electrolyte containing both compound A and compound B had obviously improved high-temperature cycle performance and high-temperature storage performance, reaching 86.5% (54.5% in Cited document 3) after 400 cycles at 45V. The capacity retention rate, capacity recovery rate and thickness expansion rate after 30 days of storage at high temperature of 60° C., reached 86.2% (51.5% in Cited document 3), 91.1% (55.3% in Cited document 3), 17.4% (65.4% in Cited document 3), respectively, and the 0.2C Discharge Efficiency (−20° C.) was 74.4-75.1% (75.3% in Cited document 3). It can be seen that the synergistic effect of the compound A and the compound B can obviously improve the high-temperature cycle performance and the high-temperature storage performance of the battery. Meanwhile, the combination of the compound A and the compound B has no obvious influence on the battery impedance, so that batteries made of the lithium ion non-aqueous electrolyte have better low-temperature performance.

Comparing the Embodiment 10 and Comparative Example 4, in the lithium ion non-aqueous electrolyte of Embodiment 10 and Comparative Example 4, the additive composition and proportion of Compound A are the same (FEC/PC/ Methyl 2,2,2-trifluoroethyl carbonate=2/1/1), however, Comparative Example 4 was not added with Compound B, and Embodiment 10 was added with Compound B. The results showed that compared with Comparative Example 4 to which only compound A was added, the battery made of lithium ion non-aqueous electrolyte containing both compound A and compound B had obviously improved high-temperature cycle performance and high-temperature storage performance, reaching 73.2% (45.2% in Cited document 4) after 400 cycles at 45V. The capacity retention rate, capacity recovery rate and thickness expansion rate after 30 days of storage at high temperature of 60° C., reached 77.7% (44.1% in Cited document 4), 83.2% (50.2% in Cited document 4), 30.5% (76.2% in Cited document 4), respectively, and the 0.2C Discharge Efficiency (−20° C.) was 73.8% (74% in Cited document 4). It can be seen that the synergistic effect of the compound A and the compound B can obviously improve the high-temperature cycle performance and the high-temperature storage performance of the battery. Meanwhile, the combination of the compound A and the compound B has no obvious influence on the battery impedance, so that batteries made of the lithium ion non-aqueous electrolyte have better low-temperature performance.

Comparing the Embodiments 11-13 and Comparative Example 5-7, in the lithium ion non-aqueous electrolyte of Embodiments 11-13 and Comparative Example 5-7, the additive composition and proportion of Compound A are the same (DFEA/PC/DEC/EC=1/1/1/1), moreover, they were added with the same amount of LiBOB, VC and PS. However, the Comparative Examples 5-7 were not added with Compound B, and Embodiments 11-13 were added with Compound B. The results showed that, compared with Comparative Examples 5-7, the battery made of lithium ion non-aqueous electrolyte of Embodiment 11-13 had obviously improved high-temperature cycle performance and high-temperature storage performance, reaching 80.1% (65.4% in Cited document 5) after 400 cycles at 45° C. The capacity retention rate, capacity recovery rate and thickness expansion rate after 30 days of storage at high temperature of 60° C., reached 82.5% (63.5% in Cited document 5), 87.6% (66.6% in Cited document 5), 17.8% (48.5% in Cited document 5), respectively, and the 0.2C Discharge Efficiency (−20° C.) was 74.4% (73.4% in Cited document 5). It can be seen that the synergistic effect of the compound A and the compound B can obviously improve the high-temperature cycle performance and the high-temperature storage performance of the battery. Meanwhile, the combination of the compound A and the compound B has no obvious influence on the battery impedance, so that batteries made of the lithium ion non-aqueous electrolyte have better low-temperature performance.

TABLE 3

| | Total weight percentage, composition and weight ratio of the solvent | Additive and weight percentage |
|---|---|---|
| Embodiment 14 | Total weight percentage: 85.5% FEC/PC/DEC = 2/1/1 | Compound 1: 2% |
| Embodiment 15 | Total weight percentage: 85.5% DFEA/PC/DEC/EC = 1/1/1/1 | Compound 1: 2% |
| Embodiment 16 | Total weight percentage: 85.5% FEC/PC/DFEA = 2/1/1 | Compound 1: 2% |
| Embodiment 17 | Total weight percentage: 85.5% FEC/PC/Methyl 2,2,2-trifluoroethyl carbonate = 2/1/1 | Compound 1: 2% |
| Comparative example 8 | Total weight percentage: 87.5% FEC/PC/DEC = 2/1/1 | |
| Comparative example 9 | Total weight percentage: 87.5% DFEA/PC/DEC/EC = 1/1/1/1 | |
| Comparative example 10 | Total weight percentage: 87.5% FEC/PC/DFEA = 2/1/1 | |
| Comparative example 11 | Total weight percentage: 87.5% FEC/PC/Methyl 2,2,2-trifluoroethyl carbonate = 2/1/1 | |

The test results of Embodiments 14-17 and Comparative examples 8-11 are shown in Table 4 below.

TABLE 4

| | The 200th cycle capacity retention rate at 45° C. | After 30 days storage at high temperature of 60° C. | | | 0.2 C Discharge Efficiency (−20° C.) |
|---|---|---|---|---|---|
| | | Capacity retention rate | Capacity recovery rate | Thickness expansion rate | |
| Embodiment 14 | 82.3% | 75.2% | 80.9% | 31.3% | 78.3% |
| Embodiment 15 | 71.9% | 65.6% | 70.1% | 35.9% | 78.0% |
| Embodiment 16 | 84.3% | 75.3% | 80.5% | 30.3% | 79.0% |
| Embodiment 17 | 76.1% | 70.4% | 75.5% | 32.8% | 78.6% |
| Comparative example 8 | 62.4% | 50.5% | 55.1% | 43.4% | 78.1% |
| Comparative example 9 | 54.8% | 40.9% | 45.2% | 64.4% | 77.0% |
| Comparative example 10 | 64.3% | 55.5% | 60.3% | 54.4% | 77.3% |
| Comparative example 11 | 60.4% | 49.1% | 55.2% | 65.2% | 76.0% |

Comparing the Embodiments 14-17 and Comparative Example 8-11, in the lithium ion non-aqueous electrolyte of Embodiments 14-17 and Comparative Example 8-11, the addictive compositions of compound A were FEC/PC/DEC=2/1/1, DFEA/PC/DEC/EC=1/1/1/1, FEC/PC/DFEA=2/1/1, FEC/PC/methyl 2,2,2-trifluoroethyl carbonate=2/1/1, however, Comparative Examples 8-11 were not added with Compound B, and Embodiments 14-17 were added with Compound B. The results showed that compared with Comparative Examples 8-11 to which only compound A was added, the battery made of lithium ion non-aqueous electrolyte containing both compound A and compound B had obviously improved high-temperature cycle performance and high-temperature storage performance, reaching 84.3% (64.3% in Cited document 10) after 200 cycles at 45° C. The capacity retention rate, capacity recovery rate and thickness expansion rate after 14 days of storage at high temperature of 60° C., reached 75.3% (55.5% in Cited document 10), 80.5% (60.3% in Cited document 10), 30.3% (54.4% in Cited document 10), respectively, and the 0.2C Discharge Efficiency (−20° C.) was 78.0-79% (77.3% in Cited document 10). It can be seen that the synergistic effect of the compound A and the compound B can obviously improve the high-temperature cycle performance and the high-temperature storage performance of the battery. Moreover, the combination of the compound A and the compound B has no obvious influence on the battery impedance, so that batteries made of the lithium ion non-aqueous electrolyte have better low-temperature performance.

The above descriptions are only preferred embodiments and are not intended to limit the present invention. Any modifications, equivalent substitutions and improvements made within the spirit and principles of the present invention shall be included within the scope of protection of the present invention. Also, the singular terms "a", "an" and "the" include plural reference and vice versa unless the context clearly indicates otherwise.

The invention claimed is:

1. A non-aqueous electrolyte for lithium ion battery, comprising a compound A and a compound B, wherein the compound A is at least one of compounds represented by the following structural formula I, formula II and formula III; the compound B is a compound represented by the following structural formula IV,

  ;formula I:

  ;formula II:

Formula III

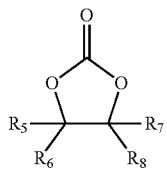

Formula IV

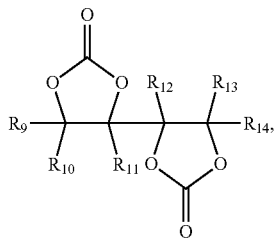

in formula I, $R_1$ is a hydrogen atom, a C1-C5 hydrocarbon group or a C1-C5 fluorohydrocarbon group, $R_2$ is a C1-C5 hydrocarbon group or a C1-C5 fluorohydrocarbon group, and at least one of $R_1$ and $R_2$ contains a fluorine atom;

in formula II, $R_3$ and $R_4$ are each independently selected from C1-C5 hydrocarbon group or C1-C5 fluorohydrocarbon group, and at least one of $R_3$ and $R_4$ contains a fluorine atom;

in formula III, $R_5$, $R_6$, $R_7$ and $R_8$ are each independently selected from hydrogen atom, fluorine atom, C1-C4 hydrocarbon group or C1-C4 fluorohydrocarbon group, and at least one of $R_5$, $R_6$, $R_7$ and $R_8$ contains a fluorine atom;

in formula IV, $R_9$, $R_{10}$, $R_{11}$, $R_{12}$, $R_{13}$ and $R_{14}$ are each independently selected from one of hydrogen atom, fluorine atom or C1-C5 group.

2. The non-aqueous electrolyte for lithium ion battery of claim 1, wherein in formula IV, the C1-C5 group is selected from a hydrocarbon group, fluorinated hydrocarbon group, oxygen-containing hydrocarbon group, silicon-containing hydrocarbon group, and cyano-substituted hydrocarbon group.

3. The non-aqueous electrolyte for lithium ion battery of claim 1, wherein in formula IV, $R_9$, $R_{10}$, $R_{11}$, $R_{12}$, $R_{13}$ and $R_{14}$ are each independently selected from a hydrogen atom, fluorine atom, methyl group, ethyl group, methoxyl group, ethyoxyl group, trimethylsiloxy group, cyano group or trifluoromethyl group.

4. The non-aqueous electrolyte for lithium ion battery of claim 1, wherein the compound B comprises one or more of compounds 1-9 represented by the following structural formulae,

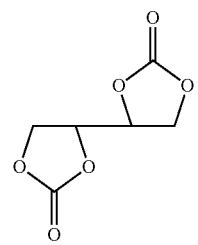
Compound 1

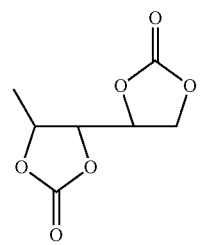
Compound 2

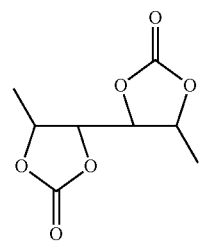
Compound 3

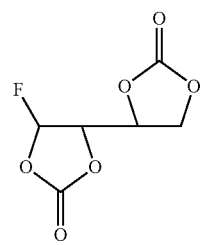
Compound 4

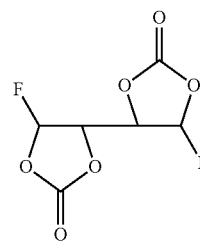
Compound 5

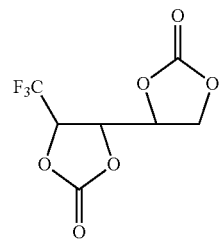
Compound 6

-continued

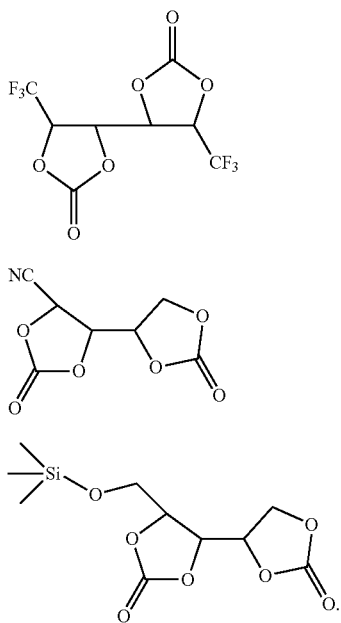

Compound 7

Compound 8

Compound 9

5. The non-aqueous electrolyte for lithium ion battery of claim 1, wherein the percentage mass content of the compound B is 0.1-5% based on the total mass of the non-aqueous electrolyte for lithium ion battery being 100%.

6. The non-aqueous electrolyte for lithium ion battery of claim 1, wherein, the compound represented by formula I is selected from one or more of $H_3CCOOCH_2CF_2H$, $H_3CH_2CCOOCH_2CF_2H$, $HF_2CH_2CCOOCH_3$, $HF_2CH_2CCOOCH_2CH_3$, $HF_2CH_2CH_2CCOOCH_2CH_3$, $H_3CCOOCH_2CH_2CF_2H$, $H_3CH_2CCOOCH_2CH_2CF_2H$, $CH_3COOCH_2CF_3$, $HCOOCH_2CHF_2$, $HCOOCH_2CF_3$ and $CH_3COOCH_2CF_2CF_2H$.

7. The non-aqueous electrolyte for lithium ion battery of claim 1, wherein the compound represented by formula II is selected from one or more of $CH_3OCOOCH_2CF_2H$, $CH_3OCOOCH_2CF_3$, $CH_3OCOOCH_2CF_2CF_3H$, $HCF_2CH_2OCOOCH_2CH_3$ and $CF_3CH_2OCOOCH_2CH_3$.

8. The non-aqueous electrolyte for lithium ion battery of claim 1, wherein the compound represented by formula III is selected from one or more of compounds 10-13 represented by the following structures,

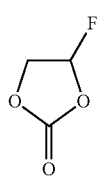

Compound 10

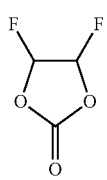

Compound 11

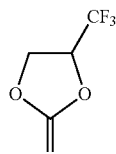

Compound 12

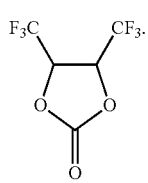

Compound 13

9. The non-aqueous electrolyte for lithium ion battery of claim 1, wherein the percentage mass content of the compound A is less than 80% based on the total mass of the non-aqueous electrolyte for lithium ion battery being 100%.

10. The non-aqueous electrolyte for lithium ion battery of claim 9, wherein the compound A is at least one of compounds represented by structural formula I, formula II and formula III, and $R_5$ in formula III is fluorine, $R_6$, $R_7$ and $R_8$ are each independently selected from hydrogen atom, fluorine atom, C1-C4 hydrocarbon group or C1-C4 fluorohydrocarbon group, and $R_6$, $R_7$ and $R_8$ cannot be hydrogen atom at the same time; or $R_5$ is C1-C4 fluorine-containing hydrocarbon group, $R_6$, $R_7$ and $R_8$ are independently selected from hydrogen atom, fluorine atom, C1-C4 hydrocarbon group or C1-C4 fluorine-containing hydrocarbon group.

11. The non-aqueous electrolyte for lithium ion battery of claim 9, wherein the compound A is fluoroethylene carbonate, and the percentage mass content of the compound A is greater than 5% and less than or equal to 80% based on the total mass of the non-aqueous electrolyte of the lithium ion battery being 100%.

12. The non-aqueous electrolyte for lithium ion battery of claim 9, wherein the percentage mass content of the compound A is 10-80%, based on the total mass of the non-aqueous electrolyte of the lithium ion battery being 100%.

13. The non-aqueous electrolyte for lithium ion battery of claim 1, wherein the lithium ion non-aqueous electrolyte further comprises at least one of unsaturated cyclic carbonate compounds and sultone compounds.

14. The non-aqueous electrolyte for lithium ion battery of claim 13, wherein the unsaturated cyclic carbonate compound comprises at least one of vinylene carbonate and vinyl ethylene carbonate;
the sultone compound is selected from at least one of 1,3-propane sultone, 1,4-butane sultone, and 1,3-propene sultone.

15. The non-aqueous electrolyte for lithium ion battery of claim 13, wherein the percentage mass content of the unsaturated cyclic carbonate compound is 0.1-5% based on the total mass of the non-aqueous electrolyte of the lithium ion battery being 100%; the percentage mass content of the sultone compound is 0.1-5% based on the total mass of the non-aqueous electrolyte of the lithium ion battery being 100%.

16. The non-aqueous electrolyte for lithium ion battery of claim 1, wherein the non-aqueous electrolyte for lithium ion battery comprises lithium salt; the lithium salt can be selected from one or more of $LiPF_6$, LiBOB and $LiBF_4$.

17. The non-aqueous electrolyte for lithium ion battery of claim 1, wherein the lithium salt content in the non-aqueous electrolyte for lithium ion battery is 0.1-15%.

18. The non-aqueous electrolyte for lithium ion battery of claim 1, wherein the non-aqueous electrolyte for lithium ion battery comprises a solvent, and the solvent is selected from at least one of vinyl carbonate, propylene carbonate, butylene carbonate, dimethyl carbonate, diethyl carbonate, methyl ethyl carbonate and methyl propyl carbonate.

19. A lithium ion battery, comprising a positive electrode, a negative electrode, a separator interposed between the positive electrode and the negative electrode, and an electrolyte, wherein the electrolyte is the non-aqueous electrolyte for lithium ion battery of claim 1.

20. The lithium ion battery of claim 19, wherein the positive electrode comprises a positive electrode active material, and the positive electrode active material is at least one of $LiNi_xCo_yMn_zL_{(1-x-y-z)}O_2$, $LiCo_xL_{(1-x')}O_2$, $LiNi_{x''}L'_{y'}Mn_{(2-x''-y')}O_4$ and $Li_zMPO_4$, wherein, L is at least one of Al, Sr, Mg, Ti, Ca, Zr, Zn, Si or Fe, $0 \le x \le 1$, $0 \le y \le 1$, $0 \le z \le 1$, $0 < x+y+z \le 1$, $0 < x' \le 1$, $0.3 \le x'' \le 0.6$, $0.01 \le y' \le 0.2$, L' is at least one of Co, Al, Sr, Mg, Ti, Ca, Zr, Zn, Si and Fe; $0.5 \le z' \le 1$, M is at least one of Fe, Mn and Co.

* * * * *